United States Patent
Aggerholm

(10) Patent No.: US 10,245,410 B2
(45) Date of Patent: Apr. 2, 2019

(54) RAPID EXCHANGE CATHETER

(75) Inventor: Steen Aggerholm, St. Heddinge (DK)

(73) Assignee: Cook Medical Technologies LLC, Bloomington, IN (US)

( * ) Notice: Subject to any disclaimer, the term of this patent is extended or adjusted under 35 U.S.C. 154(b) by 512 days.

(21) Appl. No.: 12/829,575

(22) Filed: Jul. 2, 2010

(65) Prior Publication Data
US 2011/0160834 A1    Jun. 30, 2011

(30) Foreign Application Priority Data
Jul. 2, 2009    (GB) .................................... 0911532.0

(51) Int. Cl.
| | | |
|---|---|---|
| A61M 25/00 | (2006.01) | |
| A61F 2/958 | (2013.01) | |
| A61M 25/10 | (2013.01) | |
| A61M 25/01 | (2006.01) | |

(52) U.S. Cl.
CPC ......... A61M 25/0023 (2013.01); A61F 2/958 (2013.01); A61M 25/0015 (2013.01); A61M 25/0054 (2013.01); A61M 25/10 (2013.01); A61M 2025/0183 (2013.01)

(58) Field of Classification Search
CPC .............. A61M 31/00; A61M 25/0023; A61M 25/0015; A61M 2025/0183; A61M 25/10; A61F 2/958
USPC ...................................... 604/103.04; 606/192
See application file for complete search history.

(56) References Cited

U.S. PATENT DOCUMENTS

| | | | |
|---|---|---|---|
| 5,549,552 A | | 8/1996 | Peters et al. |
| 5,830,227 A | * | 11/1998 | Fischell et al. ............... 606/194 |
| 6,066,114 A | * | 5/2000 | Goodin ............... A61M 25/104 604/103.04 |
| 6,273,879 B1 | * | 8/2001 | Keith et al. .................... 604/523 |
| 6,361,529 B1 | * | 3/2002 | Goodin ............... A61M 25/104 604/102.02 |
| 6,485,457 B1 | * | 11/2002 | Hisamatsu et al. ...... 604/102.02 |
| 6,575,958 B1 | * | 6/2003 | Happ .................. A61M 25/104 604/525 |
| 6,635,029 B1 | | 10/2003 | Venturelli |
| 6,733,486 B1 | * | 5/2004 | Lee et al. ....................... 604/525 |
| 7,273,470 B2 | | 9/2007 | Wantink |
| 7,297,134 B2 | | 11/2007 | Krivoruchko |
| 7,367,976 B2 | * | 5/2008 | Lawes ................. A61B 18/1445 606/41 |
| 8,043,256 B2 | * | 10/2011 | Hansen et al. ............. 604/96.01 |
| 2001/0037085 A1 | * | 11/2001 | Keith et al. ................ 604/96.01 |

(Continued)

FOREIGN PATENT DOCUMENTS

| | | |
|---|---|---|
| EP | 0 873 759 | 10/1998 |
| EP | 0875263 A3 | 1/1999 |

(Continued)

OTHER PUBLICATIONS

Combined Search and Examination Report from corresponding application GB0911532.0, dated Jan. 13, 2011, 4p.

*Primary Examiner* — Richard G Louis

(74) *Attorney, Agent, or Firm* — Brinks Gilson & Lione

(57) ABSTRACT

A rapid exchange catheter includes a stiff proximal tube and a relatively flexible tapered distal tube, a guide wire tube being provided in the distal tube, with an aperture for access to the guide wire lumen being provided at the junction between the distal tube and the proximal tube, the tubes being bonded together at their junction.

13 Claims, 3 Drawing Sheets

(56) References Cited

U.S. PATENT DOCUMENTS

| | | | |
|---|---|---|---|
| 2004/0019324 A1 | 1/2004 | Duchamp | |
| 2004/0054323 A1* | 3/2004 | Wantink | A61M 25/0052 |
| | | | 604/103.04 |
| 2004/0092867 A1* | 5/2004 | Murray, III | 604/103 |
| 2004/0186506 A1* | 9/2004 | Simpson | A61M 25/0009 |
| | | | 606/194 |
| 2005/0177043 A1 | 8/2005 | Windheuser | |
| 2005/0267408 A1* | 12/2005 | Grandt | A61M 25/0021 |
| | | | 604/103.04 |
| 2006/0004325 A1 | 1/2006 | Hamatake et al. | |
| 2006/0217682 A1* | 9/2006 | Stivland et al. | 604/524 |
| 2006/0259117 A1* | 11/2006 | Pal | A61F 2/95 |
| | | | 623/1.11 |
| 2009/0149808 A1* | 6/2009 | Hansen et al. | 604/103.04 |
| 2010/0217234 A1* | 8/2010 | Grovender | A61L 29/06 |
| | | | 604/523 |
| 2012/0006479 A1* | 1/2012 | Hansen et al. | 156/272.8 |

FOREIGN PATENT DOCUMENTS

| | | |
|---|---|---|
| WO | WO 2003/047679 A1 | 6/2003 |
| WO | WO 2005/118044 A1 | 12/2005 |
| WO | 2007059281 A1 | 5/2007 |
| WO | 2008005706 A3 | 1/2008 |
| WO | 2008134382 A1 | 11/2008 |

* cited by examiner

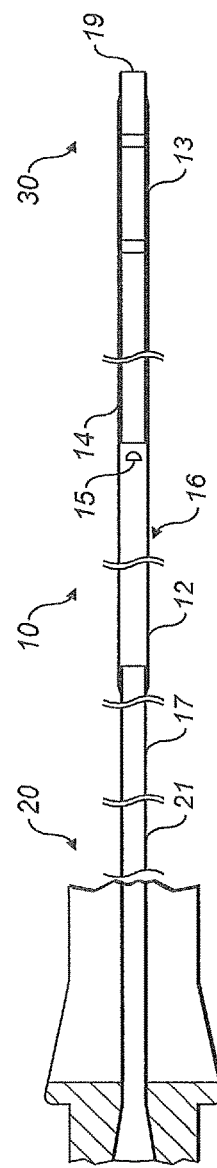
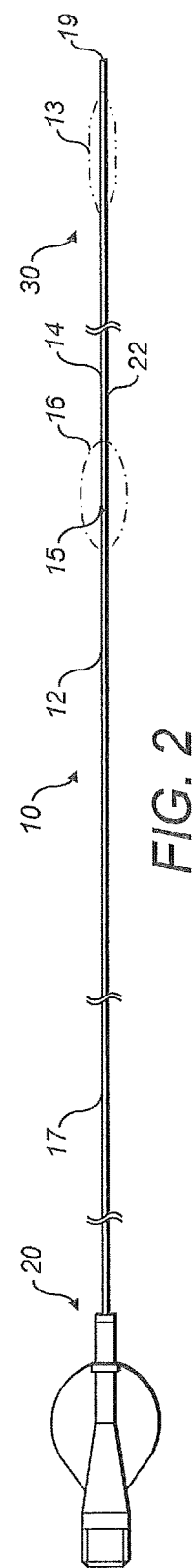
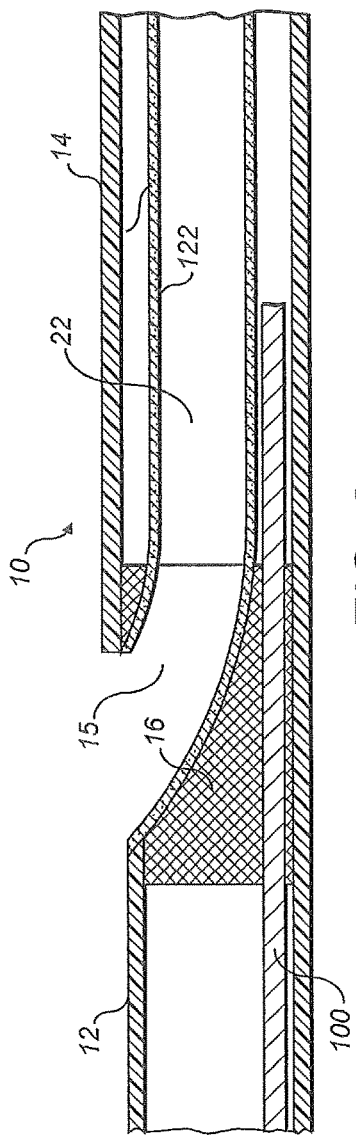

RAPID EXCHANGE CATHETER

CROSS-REFERENCE TO RELATED APPLICATIONS

This application claims priority of United Kingdom patent application Serial No. GB0911532.0, filed Jul. 2, 2009.

TECHNICAL FIELD

The present invention relates to a rapid exchange catheter. In particular it relates to a catheter that may be used in a rapid exchange system. The present invention also relates to an implant deployment assembly including a catheter.

BACKGROUND ART

Catheters have found widespread use in medical procedures, such as percutaneous transluminal coronary angioplasty (PTCA) or for delivery of an implant such as a stent, a stent-graft or an occlusion device. Most catheters are guided to the application site by sliding the catheter along a guide wire, which has been carefully advanced and arranged within the patient. During advancement of the catheter along the guide wire, it is important to keep the guide wire steady. Ordinary catheters are guided to the application site in a patient by sliding the catheter along a guide wire extending all the way through a lumen of the catheter from the proximal end to the distal end thereof. To enable the physician to hold or manipulate the guide wire during advancement of the catheter along the guide wire, it has been necessary to have an excess length of guide wire. The guide wire must hence have a length of about twice the length of the catheter, e.g. 3 m in total, which greatly complicates the procedure.

An important sub-category of catheters includes catheters of the so-called rapid exchange type, which greatly facilitate operation, especially exchange of catheters if it is found during a procedure that a different kind or size of catheter is needed for a specific purpose. In the rapid exchange catheter, the guide wire only passes through a minor part of the catheter at the distal end thereof, whereas along a majority of the catheter, the guide wire runs in parallel with the catheter. Hence it is not necessary to have an excess length of guide wire. However, the rapid exchange catheter presents some challenges, especially with regard to resistance to kinking of the catheter.

An important feature of catheters is the transmission of force, the so-called push force, from the proximal end to the distal end of the catheter. This transmission significantly affects the physician's ability to direct the distal end of the catheter into a body lumen of a patient by manipulating the proximal end thereof. Another important feature of catheters is the flexibility of the distal end to bend and conform to the body lumen wall without causing any injury to the lumen wall. Hence catheters, especially of the rapid exchange type, are commonly manufactured of a metal proximal shaft portion of relatively high stiffness and known as a "hypotube", and a relatively flexible plastics distal portion bonded to the hypotube. An abrupt change of properties between the hypotube and the distal portion, however, increases the risk of twist and kinking. Hence it is desirable to provide a good and simple transition between the relatively stiff hypotube to the relatively more flexible distal section to provide a sufficient resistance to twist and kinking while maintaining flexibility and ability to bend.

U.S. Pat. No. 6,635,029, U.S. Pat. No. 6,066,114, U.S. Pat. No. 7,273,470, and U.S. Pat. No. 7,297,134 disclose examples of rapid exchange catheters.

EP 0875263, US 2005/0177043, US 2004/0019324, WO 2008/005706, U.S. Pat. No. 5,549,552, WO 2008/134382 and WO 2007/059281 disclose deployment arrangements with tapered components, especially tapered distal tubes.

DISCLOSURE OF THE INVENTION

The present invention seeks to provide an improved implant deployment catheter.

According to a first aspect of the present invention, there is provided a rapid exchange catheter assembly comprising a proximal tube, a distal tube, an aperture located at the junction between the distal tube and the proximal tube, and a guide wire tube extending from the aperture and within the distal tube, wherein the distal tube, the proximal tube and the guide wire tube are bonded together at the junction.

The bonding is preferably achieved by heat treatment. The bonding may also be achieved by use of an adhesive.

In a preferred embodiment the distal tube includes a taper such that its proximal end has a greater diameter than its distal end.

The taper allows the distal end of the distal tube to be very flexible, and thereby able easily to negotiate tortuous vasculature. The proximal end of the distal tube is relatively stiffer, and thus enables the surgeon to transfer force exerted on the proximal end of the deployment catheter to the distal tube.

The proximal tube may include a hypotube, which may include a taper. In some embodiments it may include a hypotube and a middle tube. The middle tube may extend from the distal end of the hypotube and/or may surround at least a portion of the hypotube. Preferably the hypotube includes a tubular portion and a skived portion. In an embodiment the proximal tube includes a middle tube, the middle tube extending from the distal end of the tubular portion of the hypotube. The skived portion of the hypotube may extend across the junction between the distal tube and the proximal tube.

The hypotube is stiffer than the middle tube and the distal tube.

In an embodiment, the taper extends substantially along the entire length of the distal tube for example, along at least 90% of the length of the distal tube.

However, the distal tube may include non-tapered portions. For example, a non-tapered portion may be provided at each end of the distal tube, with the tapered portion extending therebetween.

The distal tube may have a greater diameter at its proximal end than the proximal tube has at its distal end. In an embodiment, the wall of the proximal end of the distal tube located distally of the aperture extends radially beyond the wall of the proximal tube proximal of the aperture.

The distal end of the distal tube may have an outer diameter approximately equal to 80% to 95% of the outer diameter of the proximal end of the distal tube. The distal end of the distal tube may have an outer diameter approximately equal to 80% to 90% of the outer diameter of the proximal end of the distal tube, for example, the distal end of the distal tube may have an outer diameter approximately equal to 87% of the outer diameter of the proximal end of the distal tube.

The outer diameter of the distal end of the distal tube may be approximately the same as the outer diameter of the distal end of the proximal tube.

The outer diameter of the distal end of the distal tube may be approximately 2.7 Fr (0.9 mm). The outer diameter of the distal end of the proximal tube may be approximately 2.7 Fr (0.9 mm). The outer diameter of the proximal end of the distal tube may be approximately 3.1 Fr (1.03 mm).

The angle of the taper may be up to about 0.1° from the longitudinal axis of the distal tube, for example, it may be 0.006° to 0.0026°, for example 0.01° to 0.03° and/or 0.013° to 0.026°. In an embodiment, the angle of the taper is approximately 0.015°, 0.016° or 0.017°, for example.

Preferably, the proximal tube includes only a single lumen, which may be an inflation lumen. The distal tube may include a plurality of lumens, such as, for example, a guide wire lumen and an inflation lumen.

According to a second aspect of the present invention, there is provided a rapid exchange implant deployment catheter assembly comprising a distal tube extending to the distal end of the assembly and capable of carrying a balloon, a proximal tube arranged proximally of the distal tube, a guide wire tube located within the distal tube and having proximal and distal ends, an aperture for access to the proximal end of the guide wire tube, the aperture being located at a junction between the distal tube and the proximal tube, the distal tube having a taper such that its proximal end has a greater diameter than its distal end, wherein the distal tube, the proximal tube and the guide wire tube are bonded together at the junction.

According to a third aspect of the present invention there is provided a method of manufacturing a rapid exchange catheter assembly including the steps of inserting a guide wire tube in the proximal end of a distal tube, assembling the distal tube with said proximal end thereof adjacent to the distal end of a proximal tube leaving an aperture between the ends of the tubes, and bonding the tubes together.

BRIEF DESCRIPTION OF THE DRAWINGS

An embodiment of the present invention is described below, by way of example only, with reference to the accompanying drawings, in which:

FIG. 1 is a schematic top view of a rapid exchange catheter;

FIG. 2 is a side view of a rapid exchange catheter;

FIG. 3 shows a longitudinal cross-sectional enlargement of a portion of the rapid exchange catheter of FIG. 2 during assembly thereof;

DESCRIPTION OF THE PREFERRED EMBODIMENTS

Figure 4:
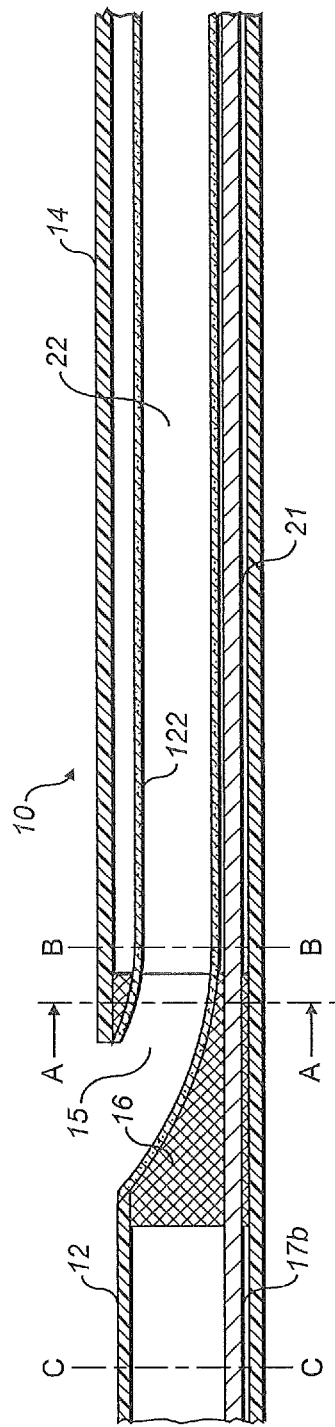
FIG. 4 shows a view similar to FIG. 3 with the catheter assembled.

It is to be understood that the Figures are schematic and do not show the various components in their actual scale. In many instances, the Figures show scaled up components to assist in the understanding of the features disclosed therein.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implant such as a stent or stent graft, the term proximal refers to a location that in use is closest to the patient's heart, in the case of a vascular implant, and the term distal refers to a location furthest from the patient's heart.

FIGS. 1 and 2 show a rapid exchange catheter. The total length of the catheter is, in some cases, about 1.4 m. The catheter 10 has a proximal end 20 and a distal end 30. The catheter 10 comprises a tubular metal shaft body 17, also known as a hypotube, made of stainless steel in this example. In other examples the hypotube 17 may be formed from Nitinol, PEEK, braiding or coils for example. An inflation lumen 21 extends through the full length of the metal shaft body 17. The hypotube 17 includes a tubular portion 17a and skived portion 17b, the skived portion 17b being arranged distally of the tubular portion 17a.

Figure 9:
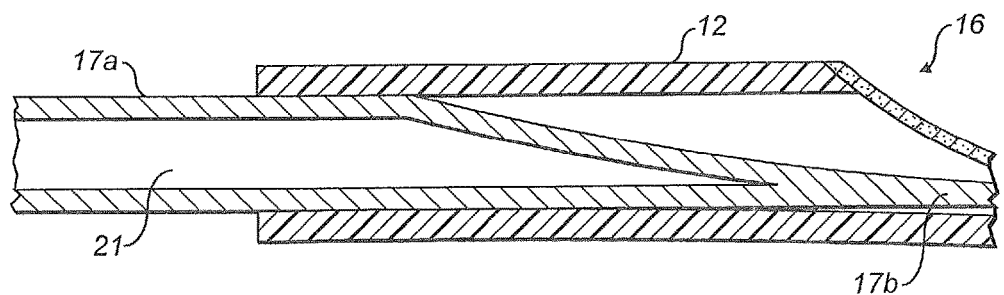
FIG. 9 shows a longitudinal cross-sectional enlargement of a portion of the rapid exchange catheter of FIG. 2.

A middle tube 12 (the hypotube 17 and the middle tube 12 together also referred to herein as a "proximal tube 12") is attached to the distal end of the tubular portion 17a of the hypotube 17, by being heat bonded to a grit-blasted or sand-blasted region of the hypotube 17. However, within the middle tube 12, the hypotube 17 changes from being tubular to being skived. Therefore, proximally of the middle tube 12 the hypotube 17 is in its tubular form, and distally of the middle tube 12 it is in its skived form. This is best illustrated in FIG. 9. In an embodiment the skived portion 17b of the hypotube 17 starts approximately 13 cm from the distal end of the hypotube 17. The inflation lumen 21 extends also through the middle tube 12. The middle tube 12 is preferably formed from nylon, PU, PE or PEBAX, although other materials are possible. The middle tube 12 acts as a transition tube between the hypotube 17 and the rapid exchange port 15.

A plastics distal end portion 14, having a length of approximately 25 cm in this embodiment, is attached to the end of the middle tube 12 by bonding. The distal tube 14 may be formed from nylon, PU, PE or PEBAX, for example. It is preferred that the distal tube 14 be formed from a material less stiff than the middle tube 12. For example, the middle tube 12 may be 25% stiffer than the distal tube 14. The distal tube 14, the middle tube 12 and the hypotube 17 are thus axially aligned, with the distal tube 14 extending from the distal end of the middle tube 12, and the middle tube extending from the distal end of the tubular portion 17a of the hypotube 17. The skived portion 17b of the hypotube 17 extends distally through the lumen of the distal tube 14, as described in greater detail below.

The plastics distal end portion 14 comprises a side port 15 for a guide wire (not shown) at a proximal side of an inflatable balloon 13, so the guide wire may extend through a lumen 22 in a tube 122 in the most distal part of the catheter to the distal end opening 19. The guide wire lumen 22 may have an outer diameter of 1.7 Fr (0.565 mm) in a preferred embodiment and is formed from an inner tube extending through the distal tube 14. In an embodiment the distal tube 14 is formed from nylon and the guide wire tube 122 is formed from PE. The region where the middle tube 12 is joined to the distal tube 14 is known as the transition zone 16. The inner tube 122 forming the guide wire lumen 22 is bonded to the distal tube at its proximal end in the transition zone 16 and is bonded at its distal end to the catheter tip. An inflation lumen 21 is provided through the transition zone 16. The skived portion 17b of the hypotube extends through the inflation lumen 21 so as to extend into the distal tube 14. The hypotube 17 is tapered as can best be seen in FIGS. 3 and 9. The distal end of the tapered skived portion 17b of the hypotube 17 terminates about 2 to 8 cm (for example, 5 to 8 cm) distally of the transition zone 16.

The term "proximal tube 12" is used herein to refer generally to the part of a deployment catheter immediately proximal of the transition zone 16. The proximal tube may therefore comprise a hypotube 17, and/or it may comprise a middle tube 12 located between a tubular portion 17a of a hypotube and the distal tube 14.

Figure 5:
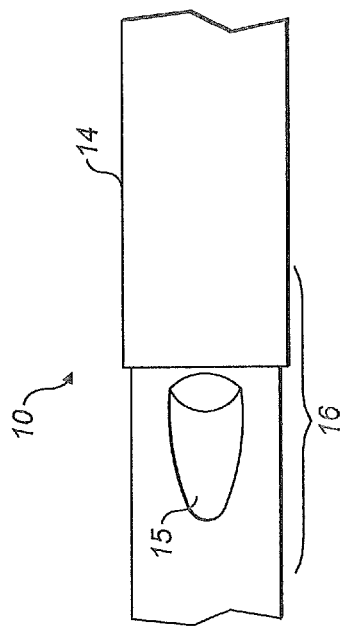
FIG. 5 shows an enlarged top view of a portion of the rapid exchange catheter of FIG. 2.

FIGS. 3, 4 and 5 show enlarged drawings of the transition zone 16 as illustrated in FIG. 2. The transition zone 16 is formed at the junction between the distal tube 14 and the proximal tube 12. In this example, the proximal tube 12 is a middle tube. A hypotube 17 is provided with its tubular portion 17a located proximally of the middle tube (not seen in these Figures). The aperture 15 for the guide wire is formed within the transition zone 16. As a result, the distal tube 14 is located distally of the aperture 15, and the proximal tube 12 is located proximally of the aperture 15.

The distal tube 14 and the middle tube 12 are simply bonded together at the transition zone 16. The bonding at the transition zone 16 is achieved by assembling the middle tube 12, the guide wire lumen 22 and the distal tube 14. The guide wire lumen 22 is arranged within the lumen of the distal tube 14. The guide wire lumen 22 and the distal tube 14 are together arranged distally of the middle tube 12. The proximal end of the guide wire lumen 22 extends through the proximal end of the distal tube 14 and initially lies on top of the middle tube 12. A mandrel (not shown in the Figures) is used in the guide wire lumen 22 to keep this open. A mandrel 100, FIG. 3, is also used to form an inflation lumen 21 through the bonding area and through which the skived portion 17b of the hypotube is inserted after the bonding process has finished and the mandrel 100 has been removed (FIG. 4). During the bonding process, heat and pressure are applied to the junction between the middle tube 12, the distal tube 14 and the guide wire lumen 22 via a shrink tube. This causes the materials to melt and become bonded to one another at the transition zone 16. This process is a very simple one-step process. The guide wire lumen 22 and the distal tube 14 may be formed by co-extrusion.

The bonding process provides a firm connection at the junction around aperture 15, which results in improved pushability of the catheter.

Figure 6:
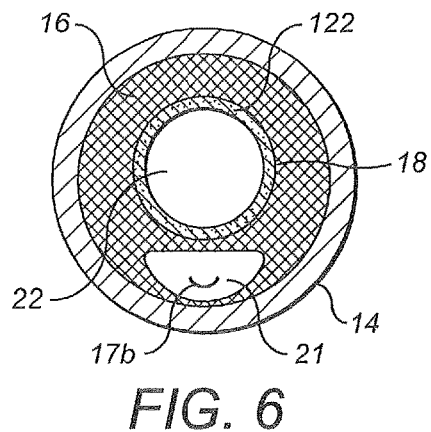
FIG. 6 is a transverse cross-section of the rapid exchange catheter of FIG. 4 on the line A-A.
Figure 7:
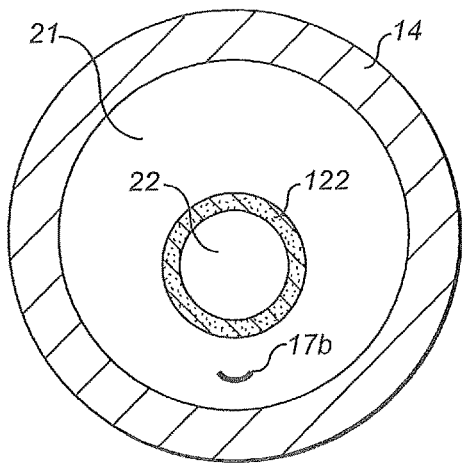
FIG. 7 is a transverse cross-section of the rapid exchange catheter of FIG. 4 on the line B-B.
Figure 8:
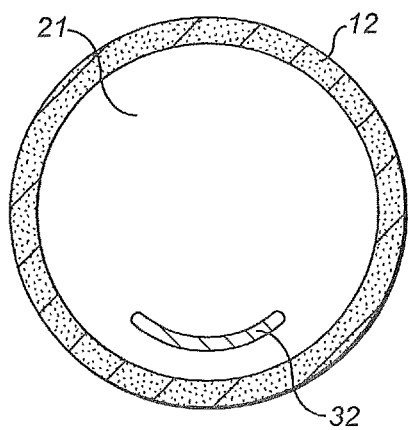
FIG. 8 is a transverse cross-section of the rapid exchange catheter of FIG. 4 on the line C-C.

The aperture 15, as indicated above, is located between the distal tube 14 and the proximal tube 12. As a result, it is not necessary to provide a guide wire aperture 15 within the proximal tube 12, which has a thicker wall than the distal tube 14, and is made of a stiffer material than the distal tube 14 (metal as opposed to a plastics material, in an example). As a result, the proximal tube 12 only has a single lumen (the inflation lumen 21) therein. Only the distal tube 14 has two separate lumens (the inflation lumen 21 and the guide wire lumen 22 extending to the aperture 15). This can best be seen in FIGS. 6 and 7.

In this example, the outer diameter of the proximal tube 12 is 2.7 Fr (0.9 mm). At its distal end, the outer diameter of the distal tube 14 is also 2.7 Fr (0.9 mm). However, as can be seen, in particular, in FIG. 3, the proximal end of the distal tube 14 has a diameter greater than the diameter of the distal end of the proximal tube 12. More particularly, in this embodiment, the outer diameter of the proximal end of the distal tube 14 is 3.1 Fr (1.09 mm). The distal tube 14 is thus tapered from its proximal end (which has a larger outer diameter than the distal end of the proximal tube 12) to its distal end (which has an outer diameter substantially equal to that of the distal end of the proximal tube 12). The taper will generally be very shallow. The angle of taper will generally be up to 0.1°. In preferred embodiments the angle may be 0.01° to 0.03°, for example approximately 0.15°, 0.16° or 0.17°. The distal tube 14 is preferably tapered substantially along the entirety of its length. However, in some embodiments a short portion at the very distal end and/or at the very proximal end may not be tapered. For example, a 25 cm distal tube 12 may include a 1 cm portion at either of each end that is not tapered. In some embodiments the taper ends at the proximal side of the balloon 13. In this embodiment, the proximal tube 12 is not tapered, and its outer diameter is thus substantially equal along its length. However, in some embodiments the proximal tube 12 may also include a taper.

The taper of the distal tube 14 results in improved pushability of the catheter. In other words, the force applied by the surgeon or clinician to the proximal tube 12 externally of the patient is better transmitted to the distal end of the distal tube 14. The tip of the distal tube 14 is relatively soft, and the distal tube 14 gets gradually stiffer along its length towards the proximal direction. This has been demonstrated in a track test, in which the catheter was placed over a guide wire and manually advanced to a laser marked starting point. A roller system then advanced and retracted the catheter 70 cm through a tortuous path three times. The guide wire was clamped down proximally during insertion and distally during retraction. The maximum and average forces to advance the tip of the catheter to a 70 cm end point were recorded.

In one test apparatus (not shown), there is provided a simulation of a tortuous blood vessel having a guide wire running therethrough. The vessel has a laser marked starting point, midpoint and end point. The results showing improved trackability of a catheter as illustrated in FIGS. 2 and 3 and as described above (Product D1) compared with a catheter not having a tapering distal tube 14 (Product D2) are given below in Table 1.

TABLE 1

| Product Name | Max Force (g) | Position (cm) | Average Force (g) |
| --- | --- | --- | --- |
| 1-D1 | 114.9795 | 70.0478 | Not determined |
| 2-D1 | 113.1311 | 65.8577 | 3.9191 |
| 3-D2 | 151.6506 | 69.5144 | 8.9566 |
| 4-D2 | 164.1598 | 69.788 | 6.4327 |
| 5-D2 | 138.3777 | 69.2333 | 8.0875 |

It can be seen that much less force is required for the tip of the above-described catheter (Product D1) to reach the 70 cm end point through a tortuous path than for Product D2.

Further advantages arise from the above-described catheter. Having the proximal end of the distal tube 14 extend radially beyond the diameter of the distal end of the proximal tube 12 allows the guide wire lumen 22 to be relatively straight. This helps to avoid kinking of the catheter between the stiffer proximal tube 12 and the more flexible distal tube 14. A sharp bend in the guide wire lumen 22 could increase resistance to movement of the guide wire through the guide wire lumen 22.

Having the proximal end of the distal tube 14 extending radially beyond the diameter of the distal end of the proximal tube, in connection with the bonded material in the transition zone 16, also provides an arrangement with improved pushability.

The described taper in the distal tube provides improved trackability. The shallowness of the taper maintains the pushability.

Having a skived portion 17b of the hypotube 17 extend through the transition zone 16 and into the distal tube 14 improves the transition between the relatively stiffer proximal tube 12 and the relatively flexible distal tube 14. This helps to avoid kinking of the catheter 10 at the transition zone 16.

The above-described embodiment makes it easier to bond the proximal tube 12 and the distal tube 14 together. A good area is provided between the proximal tube 12 and the distal tube 14 for bonding, with minimal lost bonding surface. Furthermore, the bonding can be stronger because the rapid exchange bonding is thicker on a tube having an outer diameter of 3.1 Fr (1.03 mm) than on a tube having an outer diameter of 2.7 Fr (0.9 mm).

Another advantage of the middle tube 12 having a smaller outer diameter than the proximal end of the distal tube 14 is that space is provided for the guide wire to run alongside the middle tube 12.

The skilled person will appreciate that many modifications may be made to the above-described embodiment. For example, the wall of the proximal end of the distal tube 14 may extend radially beyond the diameter of the distal end of the proximal tube 12 thereby to form the aperture 15 that provides the access point to the guide wire lumen 22. With such a modification, the axis of the aperture may be normal to the longitudinal axis of the catheter.

The distal tube 14 and the proximal tube 12 may be coated with a hydrophilic compound in order to reduce friction.

The catheter and its component parts may, of course, have dimensions that differ to those exemplified herein.

Instead of bonding using heat treatment, adhesive bonding may be employed.

Various modifications to the embodiment described above may be substituted for or combined with one another as desired. It is also to be understood that the various features of the dependent claims appended hereto may be used with one another in any desired or appropriate combination of those claims.

What is claimed is:

1. A rapid exchange catheter assembly comprising an outer proximal tube, an outer distal tube, an aperture located at the junction between the distal tube and the proximal tube, and a guide wire tube extending from the aperture and within the distal tube, wherein the distal tube, the proximal tube and the guide wire tube are bonded together at the junction, wherein the aperture is disposed within a distal end portion of the proximal tube, wherein the aperture is disposed proximal of and immediately adjacent to a proximal end of the distal tube, wherein the proximal end of the distal tube has an outer diameter that is greater than an outer diameter of the distal end portion of the proximal tube, wherein a central longitudinal axis of the distal tube is offset from a central longitudinal axis of the proximal tube at the junction so as to form an offset and stepped outer configuration, and wherein an outer surface of the distal tube along a side opposite the aperture is flush with an outer surface of the proximal tube at the junction, and wherein the proximal tube includes a hypotube comprising a tubular portion and a skived portion, the tubular portion having a constant diameter and extending to a proximal end of the assembly, the skived portion extending distally of the tubular portion, the skived portion of the hypotube extending across the junction between the distal tube and the proximal tube, and wherein an outer surface of the distal end of the proximal tube opposite the aperture is flush with an outer surface of the proximal end of the distal tube at the junction, and wherein an outer surface of the distal end of the proximal tube adjacent to the aperture is disposed inwardly of an outer surface of the proximal end of the distal tube at the juncture.

2. A catheter assembly as claimed in claim 1, wherein the outer diameter of the distal tube at a location immediately adjacent to a distal end of the aperture is greater than the outer diameter of the proximal tube at a location immediately adjacent to a proximal end of the aperture.

3. An assembly as claimed in claim 1, wherein the distal tube includes a taper such that its proximal end has a greater diameter than its distal end.

4. A catheter assembly as claimed in claim 1, wherein an outer diameter of a distal end of the distal tube is equal to the outer diameter of the distal end portion of the proximal tube.

5. A catheter assembly as claimed in claim 3, wherein the distal end of the distal tube has an outer diameter equal to 80% to 95% of the outer diameter of the proximal end of the distal tube.

6. A catheter assembly as claimed in claim 3, wherein the distal end of the distal tube has an outer diameter equal to 80% to 90% of the outer diameter of the proximal end of the distal tube.

7. A catheter assembly as claimed in claim 3, wherein the distal end of the distal tube has an outer diameter equal to 87% of the outer diameter of the proximal end of the distal tube.

8. A catheter assembly as claimed in claim 1, wherein the outer diameter of the proximal end of the distal tube is 3.1 Fr (1.03 mm).

9. A catheter assembly as claimed in claim 1, wherein the outer diameter of the distal end of the proximal tube is 2.7 Fr (0.9 mm).

10. A catheter assembly as claimed in claim 1, wherein the outer diameter of the distal end of the distal tube is 2.7 Fr (0.9 mm).

11. A catheter assembly as claimed in claim 1, wherein the proximal tube includes an inflation lumen and the distal tube includes an inflation lumen in communication with said inflation lumen of the proximal tube.

12. A catheter assembly as claimed in claim 1, wherein the proximal tube includes a middle tube, the middle tube extending from a distal end of the hypotube.

13. A catheter assembly according to claim 12, wherein the hypotube is stiffer than the middle tube and the distal tube.

* * * * *